US010029060B2

(12) United States Patent
McCauley

(10) Patent No.: US 10,029,060 B2
(45) Date of Patent: Jul. 24, 2018

(54) OROPHARYNGEAL AIRWAY

(71) Applicant: Advanced Medical Systems, LLC, Mt. Clemens, MI (US)

(72) Inventor: Steven R. McCauley, Charlotte, NC (US)

(*) Notice: Subject to any disclaimer, the term of this patent is extended or adjusted under 35 U.S.C. 154(b) by 991 days.

(21) Appl. No.: 13/871,532

(22) Filed: Apr. 26, 2013

(65) Prior Publication Data

US 2014/0323896 A1 Oct. 30, 2014

(51) Int. Cl.
*A61M 16/00* (2006.01)
*A61M 16/04* (2006.01)
*A61B 5/083* (2006.01)
*A61B 5/097* (2006.01)
*A61M 16/08* (2006.01)

(52) U.S. Cl.
CPC ....... *A61M 16/0486* (2014.02); *A61B 5/0836* (2013.01); *A61B 5/097* (2013.01); *A61M 16/0475* (2014.02); *A61M 16/0493* (2014.02); *A61M 16/0495* (2014.02); *A61M 16/085* (2014.02); *A61M 2202/0208* (2013.01); *A61M 2230/432* (2013.01)

(58) Field of Classification Search
CPC ............ A61M 16/0486; A61M 16/085; A61M 16/0493; A61M 16/0475; A61M 16/04; A61M 16/0477; A61M 16/0479; A61M 16/0484; A61M 16/0488; A61M 16/0495; A61M 16/049; A61B 5/097
USPC .................................................. 128/200.26
See application file for complete search history.

(56) References Cited

U.S. PATENT DOCUMENTS

| 1,498,810 | A | | 6/1924 | Poe |
| 2,127,215 | A | | 8/1938 | Gwathmey |
| 3,756,244 | A | | 9/1973 | Kinnear et al. |
| 4,683,879 | A | | 8/1987 | Williams |
| 4,919,126 | A | | 4/1990 | Baildon |
| 5,287,848 | A | | 2/1994 | Cubb et al. |
| 5,313,939 | A | * | 5/1994 | Gonzalez .............. A61M 16/04 128/200.14 |
| 5,976,072 | A | * | 11/1999 | Greenberg ........ A61M 16/0493 128/207.14 |
| 6,098,617 | A | * | 8/2000 | Connell ................ A61M 16/04 128/200.26 |

(Continued)

*Primary Examiner* — Bradley Philips
(74) *Attorney, Agent, or Firm* — Panagos Law Group; Dan Checkowsky; Bill Panagos

(57) ABSTRACT

An oropharyngeal device positionable within an airway of a patient may include a hollow body having a proximal end positionable adjacent the patient's mouth and an opposite distal end positionable adjacent and spaced from the patient's epiglottis. The body includes a center channel extending from the proximal end to the distal end of the body. The oropharyngeal device may include a supply passage for delivering oxygen to the patient. The supply passage may include at least one of a discharge port fluidly connecting the supply passage to an exterior region of the oropharyngeal device and a discharge port fluidly connecting the supply passage to the center channel. The discharge ports may be positioned along a wall of the body between the distal and proximal ends. The oropharyngeal device may include a sensing passage for sampling a patient's respiratory composition positioned adjacent the distal end of the body.

13 Claims, 3 Drawing Sheets

(56) References Cited

U.S. PATENT DOCUMENTS

| | | | |
|---|---|---|---|
| 6,102,041 A * | 8/2000 | Boussignac | A61M 16/00 128/207.15 |
| 6,256,524 B1 | 7/2001 | Walker et al. | |
| 6,568,388 B2 | 5/2003 | Christopher | |
| 7,278,420 B2 | 10/2007 | Ganesh et al. | |
| 2002/0108610 A1 | 8/2002 | Christopher | |

* cited by examiner

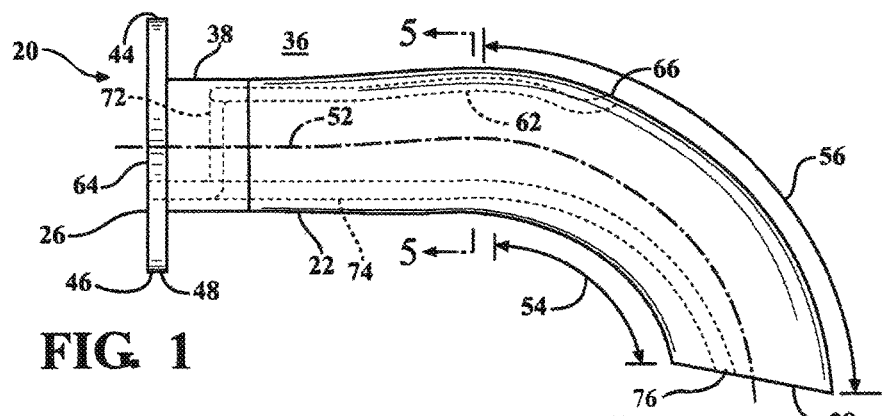
FIG. 1
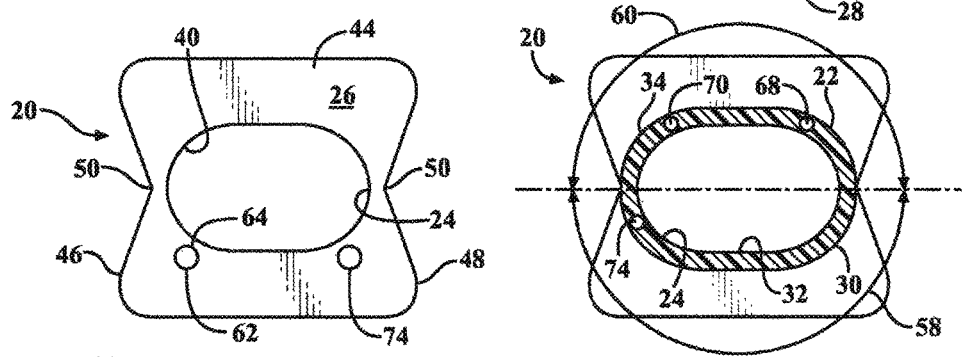
FIG. 2  FIG. 5
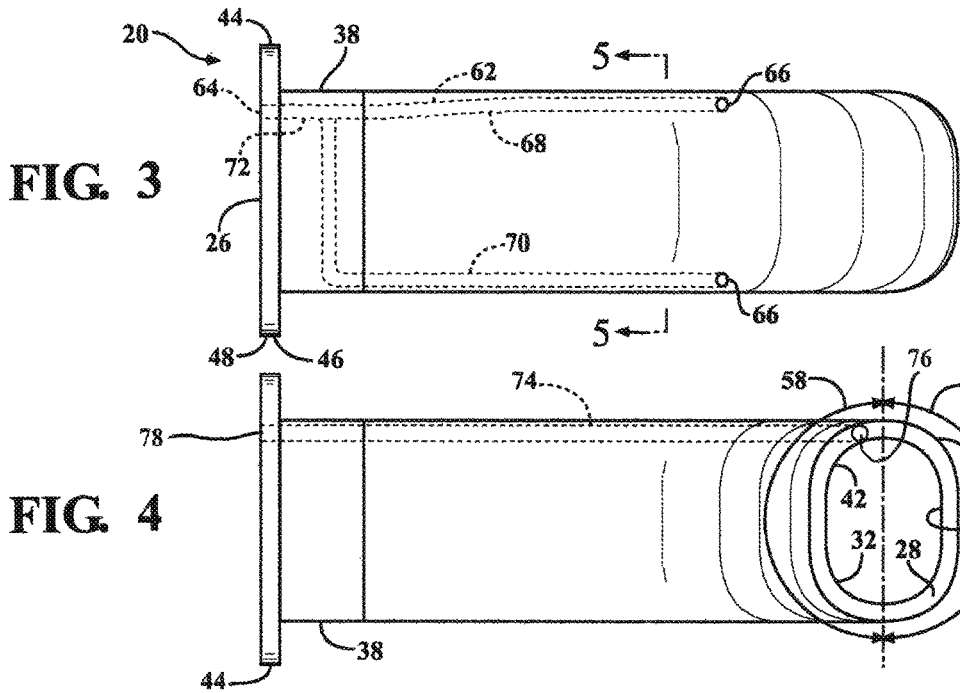
FIG. 3
FIG. 4

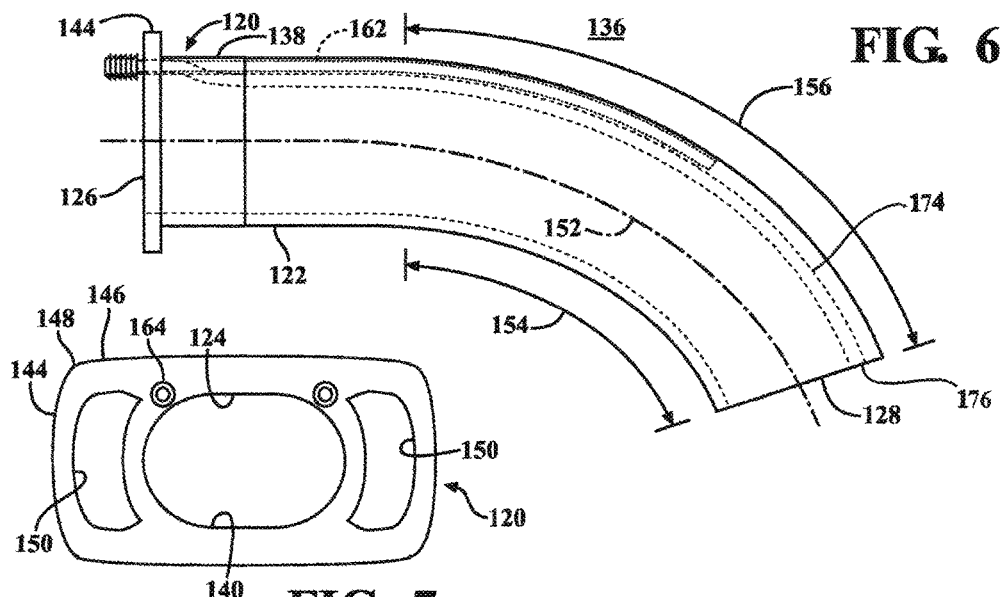
FIG. 6
FIG. 7
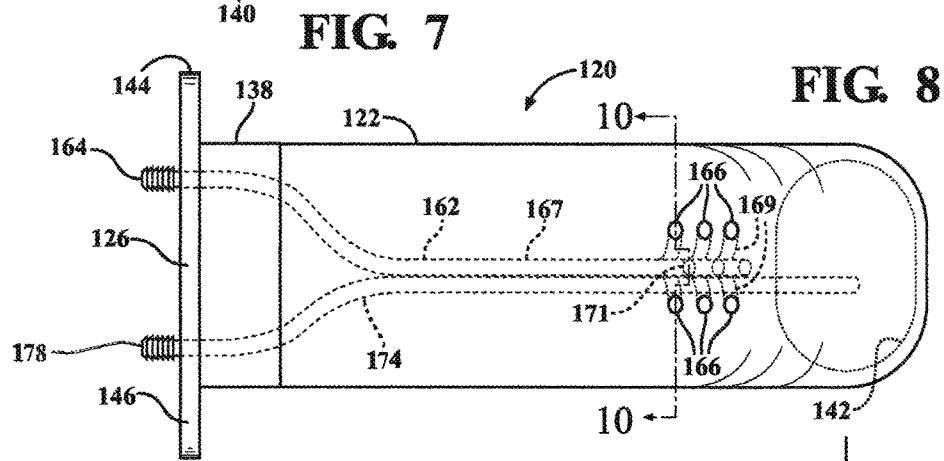
FIG. 8
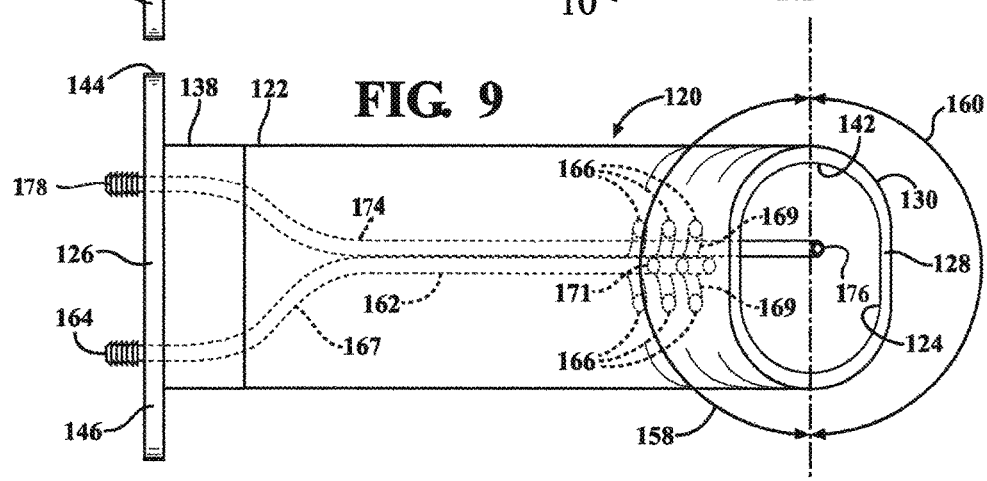
FIG. 9

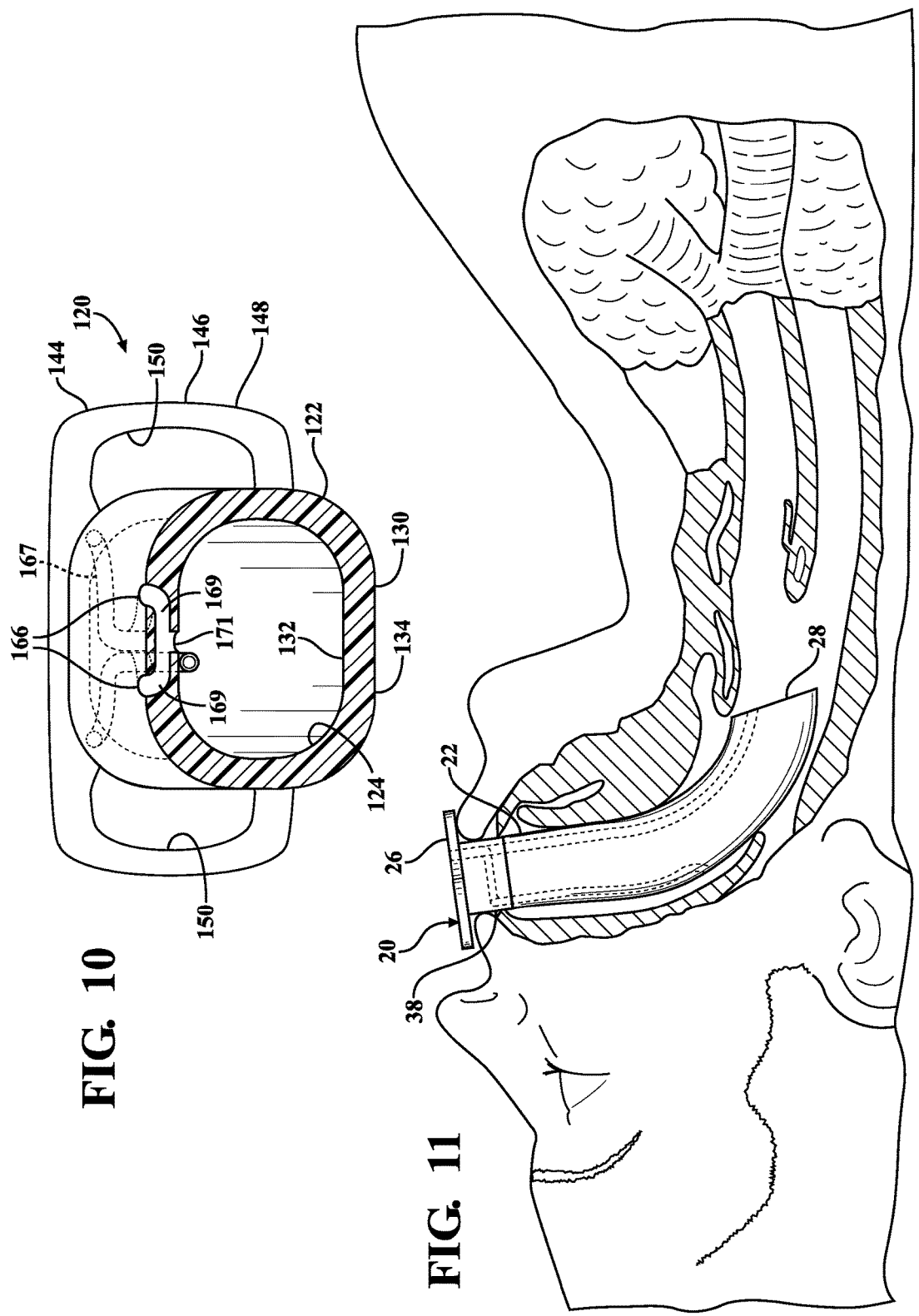

OROPHARYNGEAL AIRWAY

BACKGROUND

Respiration is the physiologic process of providing $O_2$ to cells to fuel metabolic processes and provides a means of expelling $CO_2$ from the human body as a bi-product of metabolism. The effectiveness of human respiration is controlled by the availability of oxygen, a patient airway, and the tidal volume and respiratory rate of the individual. Spontaneous respiration is a function of the tidal volume of the individual and is controlled by the particular physiology of the individual based on factors such as physical condition, trauma and medication. Ambient available $O_2$ is generally sufficient for a healthy and alert individual. However, as the individual's condition becomes impaired through disease, trauma or anesthesia, the airway may become partially obstructed and respiratory impairment may occur. As a result it may become necessary to provide supplemental $O_2$ as well as an artificial means to maintain a patient airway to control and maintain tidal volume.

The measurement of $CO_2$ upon expiration, including a capnogram waveform, is valuable to monitor the respiratory system. Capnography may provide information about $CO_2$ production, pulmonary perfusion, alveolar ventilation, respiratory patterns, and elimination of $CO_2$ from the body. Measurement of end tidal $CO_2$ ($ETCO_2$) may be obtained using an aspirating lumen that draws a $CO_2$ sample at a point determined by the device used to maintain respiratory integrity.

During anesthetic management of diagnostic and therapeutic procedures, with spontaneous respiration or controlled ventilation, an airway may be utilized to prevent obstruction. In addition, trauma or other disease processes may be treated with an airway device.

Insertion and use of an airway may cause mechanical irritation of the patient's oropharynx. Upon insertion of an airway, the health care provider must navigate the structures of the oropharynx to properly position the airway. Depending on the skill of the health care provider and the particular anatomy of the patient, damage to and or irritation of the tissues may occur. It is desired to provide an airway, which by design, will promote good practice and which makes installation of the airway easier and will be better tolerated by the patient. This requires thoughtful design of the shape and dimension of the airway as well as embodiment of materials which have a smooth finish and sufficient rigidity so that insertion and the subsequent retention of tissue may be optimized.

Anesthetic management of a patient may involve spontaneous respiration. Notwithstanding this spontaneous respiration it is beneficial to maintain an unobstructed airway during sedation and spontaneous ventilation. $O_2$ may be supplied through a nasal cannula, which may be placed as designed, or in some cases taped or wrapped around the oral airway. This supply is not optimal for a number of reasons, including availability for respiration due to physical features of the respiration flow in and around the mouth and nose. The optimal location for the release of $O_2$ is where it will be stored and then totally inspired by the patient. This would tend to dictate locating the distal point of $O_2$ discharge within the oropharynx.

The measurement of $CO_2$ through Capnography is utilized as a measure of respiratory integrity of a patient undergoing anesthetized procedures or who is otherwise obtunded. The wave patterns are of primary interest and changes in these wave patterns can mean a number of things to the healthcare provider. It is helpful to the practitioner that this measurement is in and at a point in the patients' respiratory stream where the sampling of $CO_2$ is derived in a consistent manner.

Likewise, $O_2$ should be delivered in a manner which optimizes the saturation under low pressure oxygenation of the patient. This is accomplished through an integrated connection to $O_2$ supply and delivered at a distal point which will optimize and utilize the structure within the oropharynx to create a volume of $O_2$ so that saturation upon inhalation will be provided.

BRIEF DESCRIPTION OF THE DRAWINGS

The various features, advantages and other uses of the present apparatus will become more apparent by referring to the following detailed description and drawings in which:

FIG. 1 is a side view of the exemplary oropharyngeal airway including a conduit for delivering oxygen to the patient and a separate conduit for detecting end tidal $CO_2$ levels;

FIG. 2 is an end view of the oropharyngeal airway of FIG. 1 viewed from an end of the oropharyngeal airway that is positionable adjacent the patient's mouth opening;

FIG. 3 is a top view of the oropharyngeal airway of FIG. 1 illustrating an exemplary routing scheme for the oxygen supply conduits;

FIG. 4 is a bottom view of the oropharyngeal airway of FIG. 1 illustrating an exemplary routing scheme for the conduit used to monitor end tidal $CO_2$ levels;

FIG. 5 is a cross-sectional view of the oropharyngeal airway of FIG. 1 taken along section-line 5-5 of FIG. 1;

FIG. 6 is a side view of an alternately configured exemplary oropharyngeal airway including a conduit for delivering oxygen to the patient and a separate conduit for detecting end tidal $CO_2$ levels;

FIG. 7 is an end view of the oropharyngeal airway of FIG. 6;

FIG. 8 is a top view of the oropharyngeal airway of FIG. 6 illustrating an exemplary routing scheme for the oxygen supply conduits;

FIG. 9 is a bottom view of the oropharyngeal airway of FIG. 6 illustrating an exemplary routing scheme for the conduit used to monitor tidal $CO_2$ levels;

FIG. 10 is a cross-sectional view of the oropharyngeal airway of FIG. 6 taken along section-line 10-10 of FIG. 8; and FIG. 11 illustrates an exemplary oropharyngeal airway positioned in a patient's mouth cavity and extending into the oropharynx.

DETAILED DESCRIPTION

Disclosed herein are exemplary configurations of a oropharyngeal airway that may be used to help maintain an open airway in a patient and With reference to FIGS. 1-5 and 11, an exemplary oropharyngeal airway 20 includes a hollow generally tubular-shaped body 22. A center channel 24 extends lengthwise through the body 22 between a proximal end 26 and a distal end 28, and is open at both ends. The body 22 may include a wall 30 having an inner surface 32 at least partially defining the center channel 24 and an opposite exterior surface 34 delineating an exterior region 36 of the oropharyngeal airway 20. The wall 30 separates the center channel 24 from the exterior region 36 of the oropharyngeal airway 20.

The body 22 may include a bite block 38 located at the proximal end 26 of the body 22. The bite block 38 may be configured as a separate component or integrally formed with the body 22. An opening 40 in the bite block 38 fluidly connects the proximal end 26 of the center channel 24 to the exterior region 36 of the oropharyngeal airway 20, and an opposite opening 42 fluidly connects the distal end 28 of the center channel 24 to the exterior region 36. The center channel 24 extends entirely through the body 22, including the bite block 38, to form a generally uninterrupted fluid path between the proximal end 26 and the distal end 28.

With continued reference FIGS. 1-5 and 11, the oropharyngeal airway 20 may include a flange 44 extending generally radially outward from the body 22. The flange 44 may be located generally in the vicinity of the proximal end 26. The flange 44 may have a generally planar configuration, for example, as illustrated in the drawing figures, or may have a non-planar contour, which may enable the flange to conform more closely to a patient's anatomical features.

An edge 46 defines an outer circumference 48 of flange 44. The outer circumference 48 may be configured to in include various contours. For example, the flange 44 may have a generally rectangular shape when viewed from a perspective perpendicular to the plane of the flange, such as illustrated in FIGS. 2 and 5. The outer circumference 48 may include one or more notched regions 50 that may provide an opening for inserting various medical apparatus, such as tubes, sensors, and fiber optic airway scopes.

The body 22 may be configured to include various cross-sectional profiles. For example, the body 22 may include a generally oval cross-sectional shape, for example, as illustrated in FIG. 5. Other cross-sectional shapes may also be employed. The body 22 may have a generally uniform cross-sectional shape along its entire axial length, or be configured to include a cross-section that varies.

The body 22 may be curved along its longitudinal axis 52 to enable the oropharyngeal airway 20 to generally conform to the curvature of the patient's oral cavity and oropharynx. With the oropharyngeal airway 20 disposed within the patient's oral cavity, an inside curved region 54 of the body 22 may be positioned generally adjacent the patient's tongue and an outside curved region 56 may be positioned generally adjacent the patient's palate. For purposes of discussion, the inside curved region 54 extends along a lower half 58 of the body 22 (see FIGS. 4 and 5) and the outside curved region 56 extends along an upper half 60 of the body 22. The upper and lower halves 58 and 60 of the body 22 are located on diametrically opposite sides of the body 22. The outside curved region 56 extends over the upper half 60 of the body 22 and the inside curved region 54 extends over the lower half 54 of the body 22.

The length of the oropharyngeal airway 20 may be varied to accommodate different patient anatomies. For example, a child may require a smaller oropharyngeal airway than an adult. For purposes of discussion, the length of the oropharyngeal airway corresponds to a distance between the proximal end 26 and the distal end 28 measured along the longitudinal axis 52. Generally, the oropharyngeal airway 20 may be sized so that the distal end 28 of the body 22 is positioned adjacent the patient's epiglottis when the oropharyngeal airway 20 is fully inserted into the patient's oral cavity. The oropharyngeal airway 20 may be considered fully inserted into the patient when the flange 44 is positioned adjacent the patient's oropharyngeal inlet (mouth opening). With the oropharyngeal airway 20 fully inserted into the patient's respiratory tract, the distal end 28 of the body 22 is superior to the epiglottis so as to avoid contacting the epiglottis, which may cause unnecessary stimulation.

The oropharyngeal airway 20 may be made from a variety of materials, including plastic materials, rubber and metal. The oropharyngeal airway 20 may be constructed from a single material or a combination of materials. For example, the body 22 may be made from a flexible rubber material that may allow its shape to be elastically distorted, which may facilitate insertion of the oropharyngeal airway 20 into the patient and minimize irritation and/or damage to the surrounding tissue. The body 22 may also be constructed from a rigid or semi-rigid plastic material that may provide support for the surrounding tissue. Reinforcing materials, such as metal, may be strategically located within the device to help optimize stiffness. The bite block 38 may be constructed from a generally rigid material, such as a plastic material, which may help prevent the center channel from being partially or fully closed off were the patient to bite down on the bite block. A plastic material may also be less susceptible to damage from the patient's teeth than a softer material.

Oxygen saturation levels in an alert healthy individual are adequately maintained by ambient oxygen levels available in air and normal respiratory mechanics. As an individual's respiratory mechanics become altered, for example, from disease, trauma, and the administration of drugs, the efficiency of respiratory mechanics can be impaired. When spontaneous respiration is anticipated, it may be necessary to supplement the patient with oxygen. This higher concentration of oxygen may be made available in a number of ways, including for example, a nasal cannula. When an airway is installed in an oral-pharyngeal position there is an opportunity to utilize the anatomic volume created by the oropharynx and nasopharynx to provide supplemental oxygen. Oxygen may be introduced so that the concentration is raised in these anatomic structures and made available in closer proximity to the glottic inlet to efficiently provide supplemental oxygen to the patient. The efficacy of oxygen delivered through the airway and around strategic sites takes advantage of the anatomical structures to provide more efficient oxygen delivery that may increase oxygen saturation at lower volumes of supplemental oxygen.

With continued reference to FIGS. 1-5, the exemplary oropharyngeal airway 20 may include one or more supply passages 62 for delivering a flow of gas, for example oxygen, to the patient. The supply passage 62 may include an inlet port 64 for receiving the gas from a supply source, and a discharge port 66 for delivering the gas to the exterior region 36 of the oropharyngeal airway 20. The inlet port 64 may be located near the proximal end 26 of the body 22 so as to be accessible when the oropharyngeal airway 20 is inserted in a patient's oral cavity. In the illustrated exemplary configuration of oropharyngeal airway 20, the inlet port 64 is located in the flange 44. The inlet port 64 may be fluidly connected to a gas source operable for selectively supplying a stream of gas to the patient through the supply passage 62. The gas source may be selectively adjusted to regulate the supply of gas to the patient. The inlet port 64 may include any of variously configured connectors for fluidly connecting the gas source to the supply passage 62, such as, for example, a barbed coupler and a luer lock fitting, as well as other connectors. The inlet port 64 is illustrated positioned at the bottom of the flange 44, but may alternatively be located at another location. Although a single inlet port 64 is shown employed in the exemplary configuration of oropharyngeal airway 20, multiple inlet ports may also be provided, which may improve gas delivery and may be beneficial when delivering differently formulated gases to the patient.

The discharge port 66 may be positioned so as to deliver a flow of gas to the exterior region 36 of the oropharyngeal airway 20 between the proximal end 26 and the distal end 28. The discharge port 66 may be positioned along the upper half 60 of the body 22 along the outside curved region 56. One or more discharge ports 66 may be employed. A single supply passage 62 may be employed in configurations having a single discharge port 66. In configurations employing more than one discharge port 66, the supply passage 62 may be divided into multiple passages for supply a flow of gas to each of the discharge ports. For example, exemplary oropharyngeal airway 20 is illustrated as including two discharge ports 66. A first fluid passage 68 may be employed to supply a flow of gas to one of the discharge ports 66, and a second fluid passage 70 may be employed to supply a flow of gas to the second discharge port 66. The first and second fluid passages 68 and 70 may be fluidly connected to the inlet port 64 by a third fluid passage 72. Alternatively, each of the discharge ports 66 may be independently fluidly connected to a separate inlet port, with a separate supply passage fluidly connecting each discharge port to its respective inlet port. Also, a subgroup of multiple discharge ports may be fluidly connected to a common inlet port, with the remaining discharge ports being fluidly connected to one or more inlet ports.

With continued reference to FIGS. 1-5, the supply passage 62 connecting the inlet port 64 to the discharge ports 66 may be incorporated into the body structure of the oropharyngeal airway 20. For example, in the illustrated exemplary configuration of oropharyngeal airway 20, the supply passage 62 is routed through the body wall 30. The supply passage 62 exits the body wall 30 through the discharge port 66 arranged along the exterior surface 34 of the wall 30. Alternatively, the supply passage 62 may by routed entirely along the exterior surface 34 or the inner surface 32 of the wall 30, or any combination thereof. Routing the supply passage 62 within the wall 30, or along the inner surface 32 of the wall 30, may help prevent the supply passage 62 from being damaged through handling or during insertion into the patient's oral cavity.

The measurement of respiratory composition is available throughout the patient's airway. In a closed breathing system, the measurement can be taken at any point within the closed system. In a spontaneous breathing patient, measurement becomes more difficult within the anatomical structures due to dilution by supra-glottic volume dilution and ambient air. There is advantage to measuring exhaled gas in close proximity to the glottic opening where the expiration product is being discharged from the lungs and lower airways, thereby minimizing dilution of exhaled gases.

With continued reference to FIGS. 1-5, the exemplary oropharyngeal airway 20 may include one or more sensing passages 74 for sampling gases expelled from a patient's lungs during expiration. The sensing passage 74 may include an inlet port 76 for receiving a sampling of the patient's exhaled air, and a discharge port 78 for fluidly connecting the sensing passage to equipment for analyzing the composition of the exhaled air. The analyzing equipment may be configured to detect the molecular composition of exhaled air, such as, for example, the level of carbon dioxide present. The inlet port 76 may be located adjacent or at the distal end 28 of the body 22. The discharge port 78 may include any of variously configured connectors for fluidly connecting the sensing passage 74 to the gas analyzing equipment, such as, for example, a barbed coupler and a luer lock fitting, as well as others. The discharge port 78 is illustrated positioned at the bottom of the flange 44, but may alternatively be located at another location. Although a single inlet port 76 is provided in the exemplary configuration of the oropharyngeal airway 20, multiple inlet ports 76 may also be employed to prevent obstruction from anatomic sites and secretions.

To help minimize a risk of the inlet port 76 being clogged by fluids that may be present in the patient's respiratory tract, the inlet port 76 may be positioned along the lower half 58 of the body 22. Locating the inlet port 76 along the bottom half 54 of the body 22 may prevent the inlet port 76 from contacting fluid that may collect at the back of the patient's pharynx.

One or more inlet ports 76 may be employed. A single sensing passage 74 may be employed in configurations having a single inlet port 76. In configurations employing more than one inlet port 76, the sensing passage 74 may be divided into multiple passages for receiving a sampling of the patient's exhaled air from each of the inlet ports. When employing multiple inlet ports 76, each inlet port may be independently fluidly connected to a separate discharge port, with a separate sensing passage 74 fluidly connecting each inlet port to its respective discharge port. This may be beneficial, for example, when utilizing separate gas analyzing equipment for detecting different molecular components present within the patient's exhaled gas. Each of the multiple inlet ports 76 may alternatively fluidly connect to a single sensing passage 74 to obtain an average reading of the multiple gas samples.

With continued reference to FIGS. 1-5, the sensing passage 74 connecting the inlet port 76 to the discharge port 78 may be incorporated into the body structure of the oropharyngeal airway 20. For example, in the illustrated exemplary configuration of the oropharyngeal airway 20, the supply passage 74 is routed through the body wall 30. The sensing passage 74 enters the body 22 at distal end 28 through the inlet port 76. Alternatively, the sensing passage 74 may by routed entirely along the exterior surface 34 or the inner surface 32 of the wall 22, or any combination thereof. Routing the sensing passage 74 within the wall 22 or along the inner surface 32 of the wall 22 may help prevent damage to the sensing passage occurring through handling or while being inserted into the patient's oral cavity.

With reference to FIGS. 6-10, an oropharyngeal airway 120 includes various alternately configured features that may be employed with the oropharyngeal airway 20 illustrated in FIGS. 1-5. The oropharyngeal airway 120 is similarly configured as oropharyngeal airway 20, and includes a hollow generally tubular-shaped body 122. A center channel 124 extends lengthwise through the body 122 between a proximal end 126 and a distal end 128, and is open at both ends. The body 122 may include a wall 130 having an inner surface 132 at least partially defining the center channel 124 and an opposite exterior surface 134 delineating an exterior region 136 of the oropharyngeal airway 120.

The body 122 may include a bite block 138 located at the proximal end 126 of the body 122. The bite block 138 may be configured as a separate component or integrally formed with the body 122. An opening 140 in the bite block 138 fluidly connects the proximal end 126 of the center channel 124 to the exterior region 136 of the oropharyngeal airway 120, and an opposite opening 142 fluidly connects the distal end 128 of the center channel 124 to the exterior region 136. The center channel 124 extends entirely through the body 122, including the bite block 138, to form a generally uninterrupted fluid path between the proximal end 126 and the distal end 128.

With continued reference FIGS. 6-10, the oropharyngeal airway 120 may include a flange 144 extending generally radially outward from the body 122. The flange 144 may be located generally in the vicinity of the proximal end 126. The flange 144 may have a generally planar configuration, for example, as illustrated in the drawing figures, or may have a non-planar contour, which may enable the flange to conform more closely to a patient's anatomical features.

An edge 146 defines an outer circumference 148 of flange 144. The outer circumference 148 may be configured to include various contours. For example, the flange 144 may have a generally rectangular shape when viewed from a perspective perpendicular to the plane of the flange, such as illustrated in FIG. 7. The outer circumference 148 may include one or more apertures 150 that may provide an opening for inserting various medical apparatus, such as tubes and sensors.

The body 122 may be configured to include various cross-sectional profiles. For example, the body 122 may include a generally oval cross-sectional shape, for example, as illustrated in FIG. 10. Other cross-sectional shapes may also be employed. The body 122 may have a generally uniform cross-sectional shape along its entire axial length, or may include a variable cross-section.

The body 122 may be curved along its longitudinal axis 152 to enable the oropharyngeal airway 120 to generally conform to the curvature of the patient's oral cavity and oropharynx. With the oropharyngeal airway 120 disposed within the patient's oral cavity, an inside curved region 154 of the body 122 may be positioned generally adjacent the patient's tongue and an outside curved region 156 may be positioned generally adjacent the patient's palate. For purposes of discussion, the inside curved region 154 extends along a lower half 158 of the body 122 (see FIG. 9) and the outside curved region 156 extends along an upper half 160 of the body 122. The upper and lower halves 158 and 160 of the body 122 are located on diametrically opposite sides of the body 122. The outside curved region 156 extends over the upper half 160 of the body 122 and the inside curved region 154 extends over the lower half 154 of the body 122.

The length of the oropharyngeal airway 120 may be varied to accommodate different patient anatomies. For example, a child may require a smaller oropharyngeal airway than an adult. For purposes of discussion, the length of the oropharyngeal airway corresponds to a distance between the proximal end 126 and the distal end 128 measured along the longitudinal axis 152. Generally, the oropharyngeal airway 120 may be sized so that the distal end 128 of the body 122 is positioned adjacent the patient's epiglottis when the oropharyngeal airway 120 is fully inserted into the patient's oral cavity. The oropharyngeal airway 120 may be considered fully inserted into the patent when the flange 144 is positioned adjacent the patient's mouth opening. With the oropharyngeal airway 120 fully inserted into the patient's oral cavity/oropharynx, the distal end 128 of the body 122 is disposed superior to the epiglottis so as to avoid direct contact with the epiglottis, which may cause unnecessary stimulation.

The oropharyngeal airway 120 may be made from a variety of materials, including plastic materials, rubber and metal. The oropharyngeal airway 120 may be constructed from a single material or a combination of materials. For example, the body 122 may be made from a flexible rubber material that may allow its shape to be elastically distorted, which may facilitate insertion of the oropharyngeal airway 120 into the patient and minimize irritation and/or damage to the surrounding tissue. The body 122 may also be constructed from a rigid or semi-rigid plastic material that may provide support for the surrounding tissue. Reinforcing materials, such as metal, may be strategically located within the device to help optimize stiffness. The bite block 138 may be constructed from a generally rigid material, such as a plastic material, which may help prevent the center channel from being partially or fully closed off were the patient to bite down on the bite block. A plastic material may also be less susceptible to damage from the patient's teeth than a softer material.

With continued reference to FIGS. 6-10, the exemplary oropharyngeal airway 120 may include one or more supply passages 162 for delivering a flow of gas, for example oxygen, to the patient. The supply passage 162 may include an inlet port 164 for receiving the gas from a supply source, and multiple exterior discharge port 166 for delivering the gas to the exterior region 136 of the oropharyngeal airway 120. The inlet port 164 may be located near the proximal end 126 of the body 122 so as to be accessible when the oropharyngeal airway 120 is inserted in a patient's oral cavity. In the illustrated exemplary configuration of oropharyngeal airway 120, the inlet port 164 is located in the flange 144. The inlet port 164 may be fluidly connected to a gas source operable for selectively supplying a stream of gas to the patient through the supply passage 162. The gas source may be selectively adjusted to regulate the supply of gas to the patient. The inlet port 164 may include any of variously configured connectors for fluidly connecting the gas source to the supply passage 162, such as, for example, a barbed coupler and a luer lock fitting, as well as other connectors. The inlet port 164 is illustrated positioned at the top of the flange 144, but may alternatively be located at another location.

The exterior discharge ports 166 may be positioned so as to deliver a flow of gas to the exterior region 136 of the oropharyngeal airway 120 between the proximal end 126 and the distal end 128. The exterior discharge ports 166 may be positioned along the upper half 160 of the body 122 along the outside curved region 156. A single supply passage 162 may be employed to deliver a flow of gas to each of the exterior discharge ports 166. The supply passage 162 may be divided into multiple passages for supply a flow of gas to each of the exterior discharge ports 166. For example, exemplary oropharyngeal airway 120 is illustrated as including six exterior discharge ports 166. Each discharge port may be fluidly connected to a primary supply passage 167 through a separate gas distribution passage 169. Additional exterior discharge ports 166 may also be employed, with each additional discharge port being fluidly connected to the primary supply passage 167 through its own distribution passage 169.

The oropharyngeal airway may also be configured to enable a flow of gas to be discharged into the center channel 124 of the body 122. For example, the supply passage 162 may include multiple interior discharge ports 171 for discharging the gas into the center channel 124. The interior discharge ports 171 may be positioned between the proximal end 126 and the distal end 128 of the body 122. The interior discharge ports 171 may be positioned along the upper half 160 of the body 122. The interior discharge ports 171 may be fluidly connected to the primary supply passage 167.

With continued reference to FIGS. 6-10, the supply passage 162 connecting the inlet port 164 to the exterior discharge ports 166 and interior discharge ports 171 may be incorporated into the body structure of the oropharyngeal airway 120. For example, in the illustrated exemplary configuration of oropharyngeal airway 120, the supply passage 162 is routed through the body wall 130. The supply passage 162 exits the body wall 130 through the exterior discharge ports 166 arranged along the exterior surface 134 of the wall 130, and the interior discharge ports 171 arranged along the inner surface 132 of the wall 130. Alternatively, the supply passage 162 may by routed entirely along the exterior surface 134 or the inner surface 132 of the wall 130, or any combination thereof.

With continued reference to FIGS. 6-10, the exemplary oropharyngeal airway 120 may include one or more sensing passages 174 for sampling gases expelled from a patient's lungs during expiration. The sensing passage 174 may include an inlet port 176 for receiving a sampling of the patient's exhaled air, and a discharge port 178 for fluidly connecting the sensing passage to equipment for analyzing the composition of the exhaled air. The inlet port 176 may be located adjacent or at the distal end 128 of the body 122. The discharge port 178 may include any of variously configured connectors for fluidly connecting the sensing passage 174 to the gas analyzing equipment, such as, for example, a barbed coupler and a luer lock fitting, as well as others.

To help minimize a risk of the sampling port 176 being clogged by fluids accumulating in the airways, multiple inlet sites may be positioned in the oropharyngeal airway, with the inlet port 176 may be positioned along the upper half 160 of the body 122. Locating the inlet port 176 along the upper half 160 of the body 122 may prevent the inlet port 176 from contacting fluid that may collect in the patient's pharynx.

With continued reference to FIGS. 6-10, the sensing passage 174 connecting the inlet port 176 to the discharge port 178 may be incorporated into the body structure of the oropharyngeal airway 120. For example, in the illustrated exemplary configuration of the oropharyngeal airway 120, the supply passage 174 is routed through the body wall 130. The sensing passage 174 enters the body 122 at distal end 128 through the inlet port 176. Alternatively, the sensing passage 174 may by routed entirely along the exterior surface 134 or the inner surface 132 of the wall 122, or any combination thereof.

While recited characteristics and conditions of the invention have been described in connection with certain embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An oropharyngeal device positionable within an airway of a patient, the oropharyngeal device comprising:
 a generally hollow body having an upper half and a lower half located diametrically opposite the upper half and a proximal end positionable adjacent the patient's mouth and an opposite distal edge positionable adjacent and spaced from the patient's epiglottis when the proximal end is positioned adjacent the mouth;
 a supply passage for delivering oxygen to the patient, the supply passage having a discharge port fluidly connecting the supply passage to an exterior region of the oropharyngeal device, wherein the discharge port is located only along the upper half of the body between the distal edge and the proximal end; and
 a sensing passage for sampling a patient's expiration, the sensing passage including an inlet port located only along the lower half of the body at the distal edge.

2. The oropharyngeal device of claim 1, wherein the body includes a wall at least partially defining an exterior surface and further defining a center channel extending from the proximal end to the distal edge of the body, the supply passage passing through the exterior surface of the body.

3. The oropharyngeal device of claim 2, wherein the supply passage is at least partially disposed within the wall.

4. The oropharyngeal device of claim 2, wherein the discharge port is defined by an opening in the exterior surface of the body.

5. The oropharyngeal device of claim 1, wherein the body includes a center channel extending from the proximal end to the distal edge of the body, the supply passage further comprising a second discharge port fluidly connecting the supply passage to the center channel.

6. The oropharyngeal device of claim 5, wherein the second discharge port is positioned along an interior surface of the body between the distal edge and the proximal end.

7. The oropharyngeal device of claim 1, wherein the discharge port of the supply passage is disposed longitudinally along a length of the body between the inlet port of the sensing passage and the proximal end of the body.

8. The oropharyngeal device of claim 1 further comprising a flange extending from the proximal end of the body, the flange including at least one aperture extending entirely through the flange and positioned between the exterior surface of the body and an outer circumference of the flange.

9. The oropharyngeal device of claim 1, wherein the body is curved along its longitudinal axis to form an inside curved region and an outside curved region located diametrically opposite the inside curved region, the discharge port being positioned along the outside curved region.

10. An oropharyngeal device positionable within an airway of a patient, the oropharyngeal device comprising:
 a generally hollow body having an upper half and a lower half located diametrically opposite the upper half and a proximal end positionable adjacent the patient's oropharyngeal inlet and an opposite distal edge positionable adjacent and superior to the patient's epiglottis when the proximal end is positioned adjacent the mouth, the body being curved along its longitudinal axis to form an inside curved region and an outside curved region located diametrically opposite the inside curved region;
 a supply passage for delivering oxygen to the patient, the supply passage having a discharge port fluidly connecting the supply passage to an exterior region of the oropharyngeal device, wherein the discharge port is only located within the upper half of the body along the outside curved region between the distal edge and the proximal end; and
 a sensing passage for sampling a patient's respiratory composition, the sensing passage including an inlet port located only along the lower half of the body at the distal edge.

11. The oropharyngeal device of claim 10, wherein the the inlet port is positioned only along the inside curved region.

12. The oropharyngeal device of claim 10, wherein the body includes a center channel extending from the proximal end of the body to the distal edge of the body, the supply passage further including a second discharge port fluidly connecting the supply passage to the center channel.

13. The oropharyngeal device of claim 10 further comprising a flange extending from the proximal end of the body, the flange including at least one aperture extending entirely through the flange and positioned between the exterior surface of the body and an outer circumference of the flange.

* * * * *